United States Patent [19]

Specht et al.

[11] Patent Number: 4,938,214

[45] Date of Patent: Jul. 3, 1990

[54] HAND HELD SURGICAL TOOL

[75] Inventors: Paul B. Specht, Wilmette; Harry P. Weinrib, Chicago, both of Ill.

[73] Assignee: Micrins Surgical Instruments, Ltd., Chicago, Ill.

[21] Appl. No.: 188,439

[22] Filed: Nov. 13, 1987

Related U.S. Application Data

[63] Continuation of PCT US87/00528, filed Mar. 12, 1987, which is a continuation-in-part of Ser. No. 847,237, Apr. 2, 1986, abandoned, which is a continuation-in-part of Ser. No. 674,379, Sep. 10, 1984, abandoned, and a continuation-in-part of Ser. No. 839,643, Mar. 13, 1986, Pat. No. 4,793,349, which is a continuation-in-part of Ser. No. 648,583, Sep. 10, 1983, abandoned.

[51] Int. Cl.$^5$ .................. A61B 17/06; A61B 17/21
[52] U.S. Cl. .................. 128/340; 128/321; 128/354; 128/305
[58] Field of Search ............ 128/340, 321, 354, 346, 128/318, 305; D24/23, 26, 27; 30/234–236, 253, 339

[56] References Cited

U.S. PATENT DOCUMENTS

| 383,733 | 5/1888 | Jenkins | 128/339 |
|---|---|---|---|
| 3,653,389 | 4/1972 | Shannon | 128/354 |
| 3,921,640 | 11/1975 | Freeborn | 128/318 |
| 3,972,333 | 8/1970 | Leveen | 128/318 |
| 4,165,745 | 8/1979 | Heifetz | 128/318 |
| 4,212,305 | 7/1980 | Lahay | 128/354 |
| 4,385,628 | 5/1983 | Straith | 128/321 |
| 4,446,866 | 5/1984 | Davison | 128/340 |
| 4,660,287 | 4/1987 | Decker | 30/339 |

FOREIGN PATENT DOCUMENTS

| 2491325 | 4/1982 | France . | |
| 2063140 | 6/1981 | United Kingdom | 30/339 |

Primary Examiner—Edward M. Coven
Assistant Examiner—Gary Jackson
Attorney, Agent, or Firm—Fitch, Even, Tabin & Flannery

[57] ABSTRACT

Disclosed is a microsurgical tool for use in microsurgery having a central cylindrical body which can be rotated by a surgeon. The body includes first and second portions joined at a closed end, and having needle points at the other end. Opposing longitudinal grooves formed in each half receive an alignment rod which maintains alignment of the tips as the portions are mated together. The portions of cooperating intermating recesses and protrusions extending in transverse directions are located adjacent the tips of the instrument. The protrusions and recesses provide a second, early alignment of the portions adjacent the tips of the instrument as the instrument is closed.

20 Claims, 3 Drawing Sheets

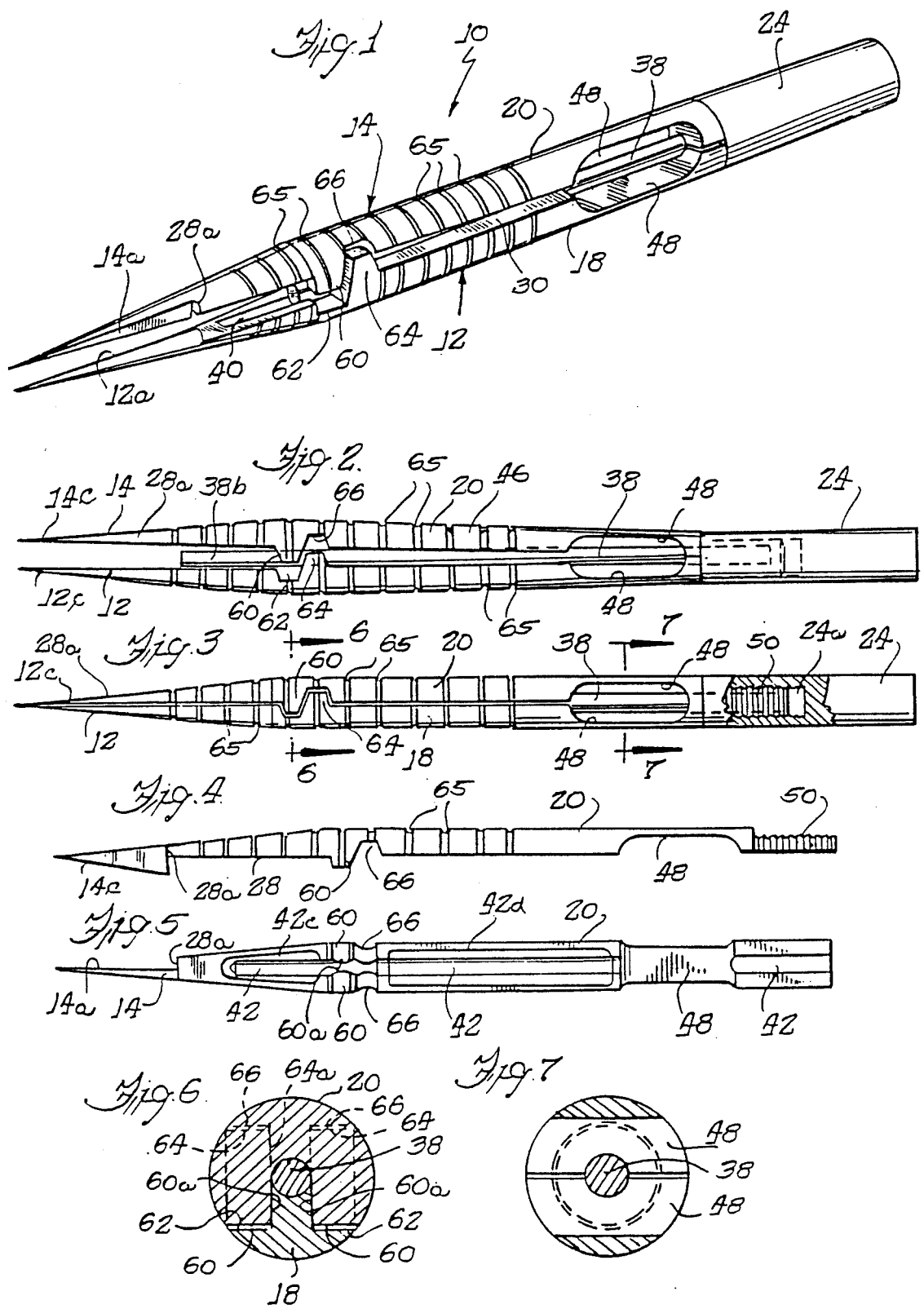

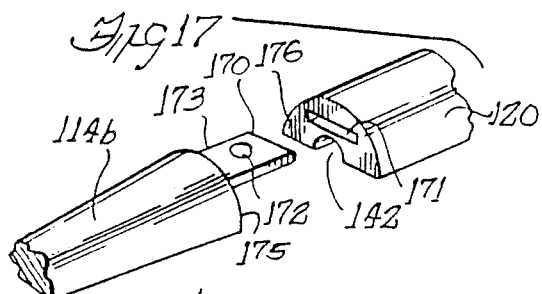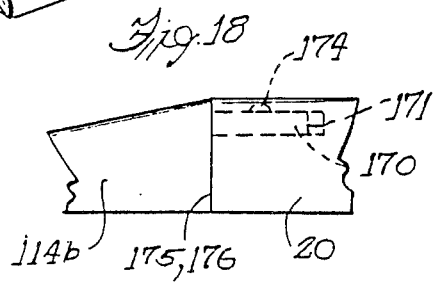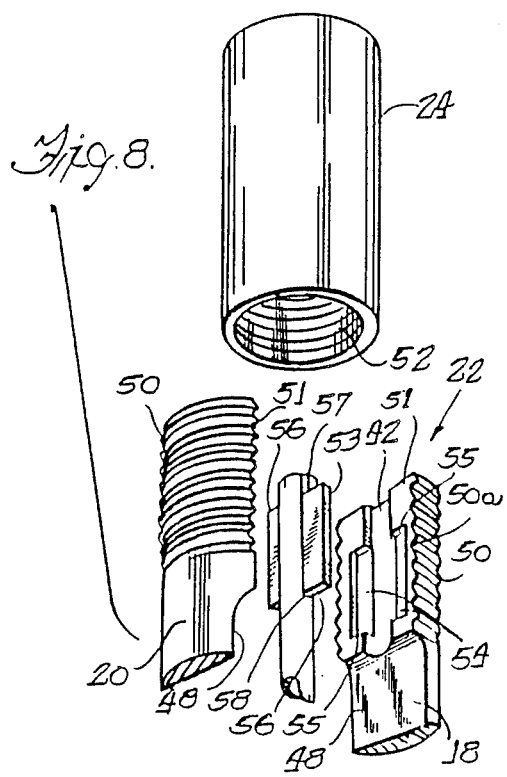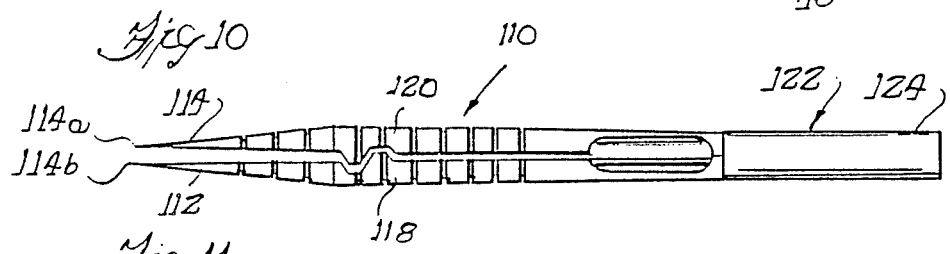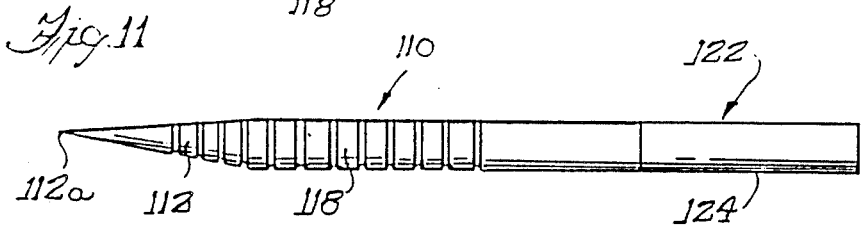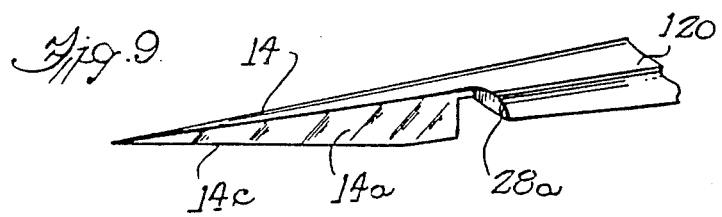

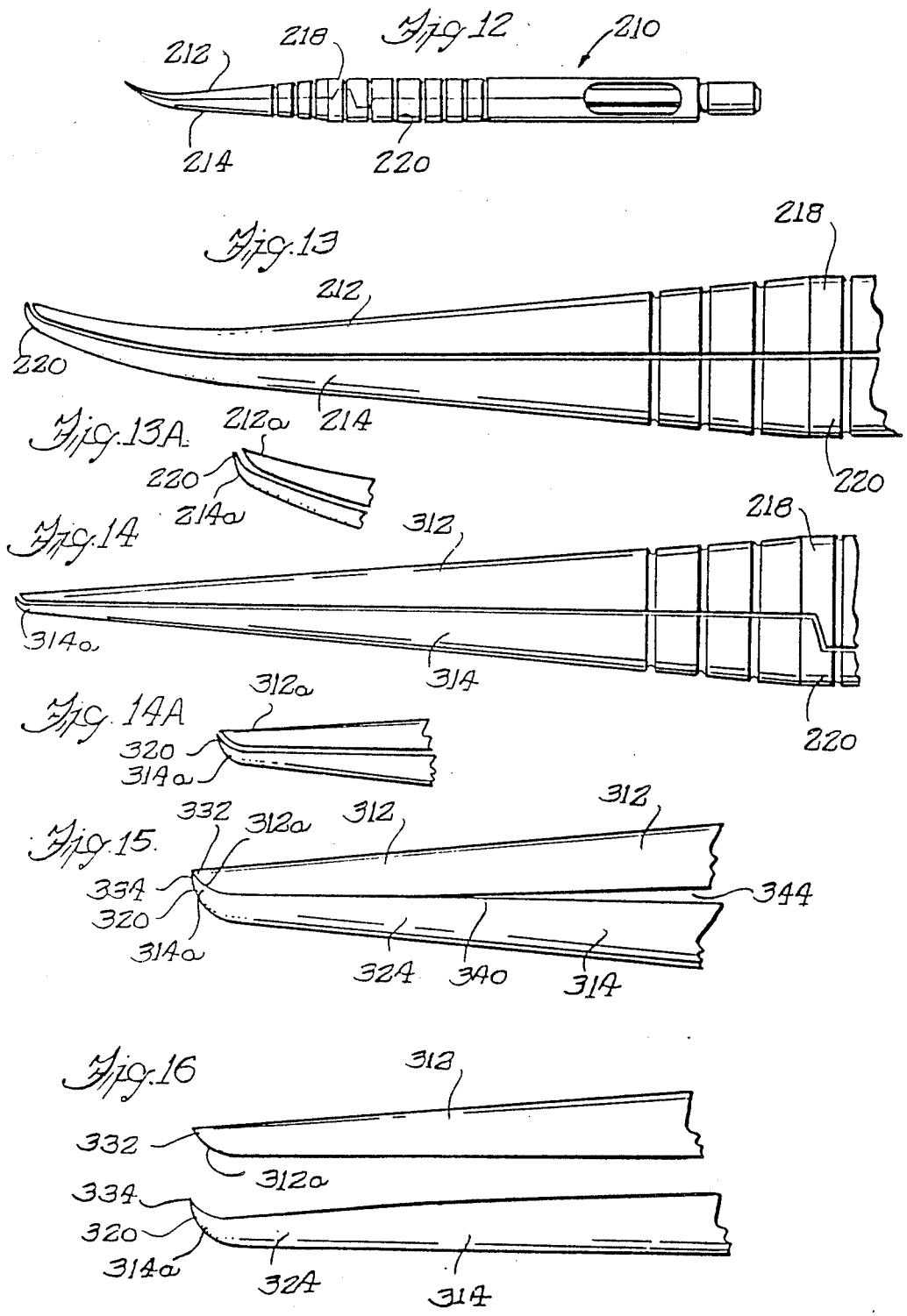

HAND HELD SURGICAL TOOL

This application is a continuation of International application PCT/US87/00528, filed Mar. 12, 1987, in which the United States was designated, which in turn is a continuation-in-part Application of pending application Ser. No. 847,237 filed Apr. 2, 1986, now abandoned, entitled "Hand-Held Surgical Tool", which is a continuation-in-part of Application Ser. No. 674,379 filed Sept. 10, 1984 now abandoned, entitled "Hand-Held Surgical Tool", and is also a continuation-in-part of Ser. No. 839,643 filed Mar. 13, 1986, U.S. Pat. No. 4,793,349, entitled "Needle Holder for Surgery", which is a continuation-in-part of Ser. No. 648,583, now abandoned, entitled needle holder for surgery filed Sept. 10, 1983.

BACKGROUND OF THE INVENTION

1. Field of Invention

This invention relates to a hand-held surgical tool used in microsurgery and, more particularly, to a microinstrument such as a forceps, scissors, needle holder, or the like which can be used with rotational microsurgery techniques.

2. Description of the Prior Art

Of the various types of surgery practiced today, microsurgical techniques are extremely demanding and pose difficulties unique to their field. For example, the size of needles, thread and body parts are microscopically small, and typically, microsurgery is performed under 20× magnification. Also, inefficiencies in the manual movement a surgeon is required to perform during an operation become an area of major concern since microsurgery requires very precise, critical movements, and the operations are quite lengthy, typically requiring hundreds if not thousands of distinct hand, wrist and arm movements.

In a broad categorization, two types of techniques, each having their own type of microsurgical instruments, are in use today. In a first category, the tools used in microsurgery are generally scissor-like instruments which have a pair of pivoted levers joined at a common pivot with a handle at one end and a pair of jaws at the other end, and which are opened and closed by moving the handle. Another similar type of hand-held instrument used in microsurgery is of the tweezer or forceps type in which the two deflectable spaced tongs are joined at one end and are brought together at the other end by finger pressure. These types of scissor action instruments are grasped by the surgeon's palm and fingers and are manipulated by turning (pronating and supinating) the surgeon's wrist. Another similar type of tool falling in this category includes flat-handled microsurgery instruments which are held by the tips of the fingers, but still require wrist pronation and supination to turn them.

Turning now to the second general category, rotational microsurgery techniques employ round-handled microsurgical instruments, the type addressed by the present invention, which can be grasped like a pencil and manipulated by rolling the thumb on the middle finger. A particular advantage in using rotational microsurgical techniques is realized since the muscles which control motion at the fingertips are more precise than those muscles which control the wrist, due to the large area of brain devoted to their control. Further, rotational techniques are less tiring, especially during operations of extended duration.

The present invention is directed to instruments of very high precision, much higher than that required for standard surgical instruments. Typically, microsurgery is performed under 20× magnification, and accordingly, any misalignment in the microsurgical tool is amplified accordingly. In addition, amplification of certain types of misalignment results from the typical pivotal mating of tool halves. The quality of tools used in microsurgery is also subject to rigorous demands by virtue of the small sizes and delicate composition of the surgical arteries and body parts manipulated by those tools. Blood vessels cut, dilated, grasped and sutured by the instruments are typically in the range of 0.5 mm in diameter. Thread employed in suturing is finer than human hair and is gossamer fine. To the human eye, unaided by magnification, the curved needles are as fine as a baby's eyelash having a diameter of about 70 microns, i.e., 0.070 millimeter. If the microsurgical needle is grasped and is bent by the forceps, then it is no longer useful. Further, the forceps is used to grasp the fine thread to assist in tying knots for a stitch. In other instances, a surgeon will grasp a curved microsurgical needle with a conventional needle holder in his dominant hand and with a forceps in the non-dominant hand he will grip and rotate the needle tip through a 90° arc. He may then release the tip and regrip the needle tip and turn it an additional arc so that the needle is properly oriented with the point up and ready for the rotational and spinning movement. The slightest opening of the tip of a forceps or scissors, for example, would render the tool very difficult, if not impractical for use in a delicate operation, especially operations of extended duration involving many hundreds if not thousands of tool manipulations.

It is easy for these fine needle-pointed tips of the microinstrument to move out of proper mating alignment, i.e., to drift apart, splay, or twist relative to one another between an opened position and a fully closed, tightly gripping position. As a result, the needle, thread, or tissue, for example, are not properly gripped, cut or held as is desired. Because of the microscopic size of needles and sutures and also because of the microscopic size of portions of the body which are being repaired, it is imperative that improved alignment arrangements be provided for forceps, scissors and other hand-held microsurgical tools. Thus, there is a need for a microinstrument which guarantees constant alignment during the full range of opening and closing of the forceps-type device and that, regardless of the position of the instrument and the direction of manipulatory forces being applied to the instrument, the ends will always come together in perfect alignment, and will not move or twist relative to one another.

There is a particular need for a microinstrument having the above improvements which can be rotated easily with finger movement rather than with wrist movement. In particular, the rotational surgical technique presents a somewhat unique problem in providing a proper alignment between tips comprising mating halves that are drawn together by a surgeon's finger pressure. A crossing over of the tips in a direction perpendicular to that of tool closure is much more likely when the rotation surgical technique is employed, since the surgeon is frequently rotating the tool while the two halves are pressed together.

In addition to providing a forceps or gripping type of microsurgical instrument, the present invention is directed to scissors which can be used in microsurgery, particularly the rotational type of microsurgical technique. Such a scissors instrument must be capable of rotation by the microsurgeon to almost any angle in that the surgeon must be able to compress the scissor tips together to form a cut in tissue or thread while at an awkward angle. Because the tips are so finely pointed in a forceps-like scissors, it is difficult to hold the scissor blades close together so that they properly shear through the tissue at such angles. Particularly, when the scissor blades are rotated away from a vertical plane (i.e., by the pronation or supination movements associated with these instruments) before compression toward one another, there is a tendency for scissor blades to twist laterally, a particularly noticeable effect under 20× magnification, thereby causing a greater spacing between the shearing edges and a more difficult cut.

As pointed out above, the duration of microsurgery operations is typically quite lengthy, e.g. 20 hours. Hence, the force to open or close the instrument, if properly set, may reduce the amount of hand fatigue. With the present invention, a predetermined biasing force may be provided to bias the tool to open as the surgeon releases his grip on the tips. Preferably, the alignment is continuous throughout the entire opening and closing range of the instrument, and should be as smooth and frictionless as possible. This is in contrast to many of the instruments currently provided to microsurgery practitioners. Typical alignment arrangements used in these instruments include a pilot pin on one part of the forceps which is in alignment with an opening on the opposite side of the forceps. Only when the forceps is in the final stages of closure, will the pin enter the associated opening to maintain alignment of the two sides of the forceps. When the instrument tips are fully open, the alignment pin is out of its associated, spaced opening. If the closing pressures of the surgeon's fingers are not exactly opposite and aligned normal to the longitudinal axis of the instrument, the tips will be out of alignment and the pin can miss the opening, thereby preventing the instrument from closing.

Microsurgical instruments are expensive because of their high precision surfaces and fine tolerances. Any unintentional impact to the tip of the tool is attended by a high probability that the tool will become damaged, perhaps rendering it incapable of further use. Therefore, it is desirable that such tools be capable of interchanging with replacement tips, especially with different tips capable of forming different operations. Thus, the precision of the mating portions comprising a microsurgical tool must be quite high. That is, the configurations of the mating portions must be reproduceable from exchangeable part to exchangeable part. At present, many microsurgical tools are hand made by skilled craftsmen. As has long been apparent in other fields, such handmade tools do not lend themselves to such interchangeability, especially an interchangeability that assures that the new tips have the necessary alignment for gripping microscopically fine microsurgical threads or needles, or for cutting.

Thus, there is a particular need for a cost-effective, accurate and precise, repeatable method of making tools used in microsurgery. Further, to assure commercial success in providing interchangeable parts used throughout the market of surgeons practicing microsurgery, a method for the automated manufacture of replaceable tool parts is needed. In particular, such automated process should ensure the proper mating of forceps and scissors tips, even tips of a very small included angle which have long and slender mating halves.

SUMMARY OF THE INVENTION

It is therefore an object of this disclosure to provide a hand-held microsurgical instrument having spaced fine pointed ends on two movable sections which are continuously guided in the full range of their opening and closing movements by a smooth operating, near frictionless alignment means therebetween.

Another object of this invention is to provide a hand-held surgical instrument having a cylindrical grasping portion which permits the tool to be easily rotated during use and which has an alignment means which does not interfere with such rotation.

Another object is to provide a hand-held surgical tool having removable and replaceable tips.

Yet another object of the present invention is to provide a hand-held microsurgical tool having multiple points of alignment along its mating parts, a first point progressing toward the tip of the instrument as the two parts are mated, and the second point providing an early mating alignment adjacent the instrument tip.

Yet another object of the present invention is to provide a scissors suitable for manipulation by rotational microsurgical techniques, which is suitable for cutting tissue and for the associated tasks of spreading tissue and dilating vessels.

This invention relates to a microinstrument or hand-held surgical instrument, such as a forceps, scissors, needle holder, or the like which is adapted for use in microsurgery and has an alignment means which provides a smooth and near-frictionless constant alignment during the full range of opening and closing of the forceps. Preferably, the alignment means comprises a cylindrical bar and a slot arrangement which is provided on the two sections of the instrument. The cylindrical bar and slot extend the major length of the instrument along the held shank portion. A portion of the cylindrical bar is always in the slot to insure alignment even when the functional end of the instrument is at the fully open position. As the instrument is closed, increasingly greater portions of the bar become seated in the slot, thus insuring even further alignment as the functional ends come together. The functional end of the tool can accommodate a variety of different tips to provide different surgical instruments. It is anticipated that the alignment arrangement and detachable tips will be used for forceps, needle holders, scissors and other surgical instruments which require alignment be maintained between the tips.

By removing and replacing or changing the functional ends, the instrument can be converted to a forceps, needle holder or scissors as desired. Also, if the instrument is dropped and the tip is damaged, the tip can be readily replaced at a tremendous cost savings, since the inexpensive tip and not the much more expensive body of the instrument can be discarded and replaced.

The surgical tool is provided with a cylindrical midportion which is grasped by the surgeon and may be rotated by mere finger movement. For example, if the tool is held between the thumb and forefinger, simply moving the thumb and forefinger produces rotation of the tool. This is important in suturing in microsurgery because the needles are so small and require numerous sutures that the surgeon can become fatigued in using a flat needle holder which requires wrist and arm movement to produce a single suture. Even if the forces applied to the cylindrical shank are skewed or applied in a fashion which would ordinarily case the tips to be misaligned, no such misalignment can occur because the alignment means always to maintains constant alignment during the full range of opening and closing.

In some of its aspects, the present invention attains many of the aforestated objects by providing a handheld microsurgical tool for use in microsurgery, which is comprised of an elongated body including a central cylindrical section having a longitudinal axis about which the body may be rotated by a surgeon. The central cylindrical section consists of first and second opposed, longitudinally extending portions joined at a closed end. Needle point ends on each of the first and second portions are located opposite from the closed end and movable toward and away from each other between closed and open positions respectively. Alignment means are provided for maintaining alignment of the needle point ends when in the open and closed positions and at all intermediate positions therebetween. The alignment means consist of an interior elongated guide member having an exterior smooth rounded surface, extending into said central cylindrical section and received in at least one of said first and second portions so as to be located within the configuration of the central cylindrical section and so as not to interfere with the rotation of the central cylindrical section of the tool.

The present invention further obtains other objects as set forth above by providing a method of making a surgical instrument suitable for use with a rotatable surgical technique. The method forms a blank having a substantially cylindrical body and a substantially conical tip at one end of the blank. External threads are then formed at one end of the blank and the blank is cut substantially along its axis to form first and second opposed portions each having a tip at their one end. An internally threaded cap is provided dimensioned to receive said other end of the blank, and the first and second portions are threadably engaged with the cap to form a tool having tips at one end which can be displaced relative to each other.

These and other objects of the disclosure, which will become apparent to those having ordinary skill in the art upon reference to the attached drawings, description and claims.

BRIEF DESCRIPTION OF THE DRAWINGS

In the drawings, wherein like elements are referenced alike,.

FIG. 1 is a perspective view of a surgical instrument embodying the novel features of the invention;

FIGS. 2 and 3 are side elevational views of the surgical instrument of FIG. 1, shown in open and closed positions, respectively;

FIG. 4 is an elevational view of one mating half of the instrument of FIGS. 1–3.

FIG. 5 is an inside plan view of one mating half of the instrument of FIGS. 1–3;

FIG. 6 is an enlarged sectional view taken generally along lines 6—6 of FIG. 3;

FIG. 7 is an enlarged cross-sectional view taken generally along the line 7—7 of FIG. 3;

FIG. 8 is an enlarged, exploded, fragmentary view of the upper end of the tool of FIG. 2;

FIG. 9 is an enlarged view of a scissor blade end of the scissors tool of FIGS. 1–8;

FIG. 10 is an elevation view of the surgical tool having a forceps end;

FIG. 11 is a view of the forceps of FIG. 10 in its closed position; and

FIGS. 12 is an elevational view of a surgical instrument according to the invention, having a tip adapted for use as a holder of microsurgical needles;

FIG. 13 is an enlarged view of the tip portion of the instrument of FIG. 12;

FIG. 13a is an even more enlarged view of the tip of the instrument of FIGS. 12 and 12;

FIG. 14 is a surgical instrument according to the present invention, similar to the needle holder of FIGS. 12–13a, but having a conical tip which is not bent or curved;

FIG. 14a is an enlarged view of the tip of the instrument of FIG. 14;

FIG. 15 is an enlarged view of the tip of the instrument of FIGS. 14, 14a shown in a completely closed position; and FIG. 16 is an enlarged view of the tip of the instrument of FIGS. 14–15, shown in an open position.

FIG. 17 is an arrangement for a removable and replaceable tip of the instrument of FIGS. 1 and 14.

FIG. 18 is an enlarged view of the upper end of the tool of FIG. 17.

DETAILED DESCRIPTION OF THE PREFERRED EMBODIMENT

As will be seen, the present invention can be employed in a variety of different microsurgical functions. For example, FIGS. 1–8 illustrate a scissors instrument 10 which, as will be seen, in addition to cutting, can be used to spread and grasp tissue, as well as dilating vessels. FIGS. 10 and 11 illustrate an embodiment of the present invention adapted to provide a a forceps instrument 110. FIGS. 12–16 illustrate a needle holder adapted for use with "micro-needles" that are as fine as a baby's eyelash, having a diameter of about 70 microns. When adapted as forceps, microsurgical instruments 110 according to the present invention are used in conjunction with the aforedescribed "micro-needles" to anastomize and to tie knots with a fine nylon thread which is attached to the needle and which is finer than a human hair and is gossamer fine.

Turning now to the first surgical instrument illustrated in the drawings, a small forceps-like scissor instrument 10 is shown in FIGS. 1–8 having an operating end 11 including first and second tips or ends 12 and 14 which are movable between the open position (shown in FIG. 2) and the closed position (shown in FIG. 3) so as to grip a microsurgical needle or thread or to sever a thread or tissue. As will be seen, alignment means 38 hold scissor blade tips 12 and 14 in precise alignment to give a close shearing action as their respective flat interior faces 12a, 14a slide past one another.

The illustrated scissor points are needle sharp having a diameter of only about 50 microns to 2 mm when the tips are closed as seen in FIG. 3. When the tips are closed one can see only a conical point on the end of the surgical tool because the inclined scissor cutting edges 12c, 14c on the leading edges of the faces 12a, 14a are aligned within the conical profile of the pointed end. The cutting edges 12c, 14c are inclined and are defined by the juncture of the inner edge of flat interior faces 12a, 14a and the adjacent edge of the conical surfaces.

With additional reference to FIG. 5, the scissor tips are carried on the half portions 18, 20 of a cylindrical body having a smooth, uninterrupted outer surface, suitable for the above-described rotational surgical technique. The half portions include flat interior surfaces 28 and 30 of the tool halves do not continue to the pointed end of the scissors tool (as they do for the forceps tool shown in FIGS. 10 and 11). Instead the flat interior surfaces 28 and 30 stop at shoulders 28a and 30a at which begins the flat blade-forming surfaces 12a, 14a which define generally triangular shape shearing tips and which extend normal to the plane of the flat surfaces 28 and 30.

Thus, as seen in FIG. 2, when the flat interior surface 30 is horizontally disposed, the triangular shearing tip face 12a (which appears on edge) extends vertically. As best seen in FIG. 1, the outer semiconical shape surface of the tip 12 extends the length of the tip. Each of the scissors tips is identical in shape.

This scissors surgeon's tool is particularly useful because it may be employed to do more tasks and to do more efficiently tasks accomplished with the large large conventional scissors which have a pivot pin and a wide handle portion requiring large hand movements to move the wide handle portions together to cause the scissors tips to do the cutting. Such wide handle scissors are impractical for doing a number of operations such as dilating vessels which can easily be done by inserting the fine pointed conical tips into the vessel. More specifically, the surgeon can, by pressing the tips together, form a very fine conical point, and can insert this fine point within the lumen of the vessel and then allow the points to spread apart to dilate the vessel. Also, it is possible to circumcise the tissue of the vessel by rotating the tool about the middle finger through short arcs cut at each of the arcs so that a 360° rotation of the tool results in a series of cuts about the circumference of the vessel. All of these cuts may be formed with an easy rotation of the tool on the fingers without having to open and close and release the scissors as in a large handled scissors. This fine pointed scissors can be turned through any angle and brought together to dissect tissue at angle without rotating the hand as the surgeon must do with the large handled conventional scissors. Thus it is possible in microsurgery to maintain much better control of the illustrated scissors without the use of the big muscles which cause the hands to shake. It can be readily seen that scissors is a much more compact instrument than the conventional large scissors currently used by microsurgeons, and also that the surgeon with fairly easy rotative movements of the scissors may cut tissue with a tool held in any of its 360° rotation positions unlike scissors which cut only when the handles are aligned vertically. Further, the scissors is particularly useful for dissecting and dilating vessels as well as cutting of tissue.

Because the points are so fine, there is the desired alignment means shown in the illustrating figures as a cylindrical bar or key 38 and keyway slots 40, 42 on the half portions 18, 20. Slots 40, 42 are preferably semicircular in cross-section, so that the cylindrical key 38 is fully received in the joined half portions 18, 20, allowing the flat interior surfaces 28, 30 to engage upon complete closing of the instrument, as shown in FIG. 3. As illustrated in FIGS. 1-8, the key 38 extends substantially the entire length of each half portion 18, 20, having a first end 38a engaged by the halves 18, 20, at their closed end 22 and having an opposed free end 38b which stops just short of shoulders 28a, 30a. Thus, the key 38 is always received in at least a portion of slots 40, 42 even if the instrument is in its open position. Further, in the preferred embodiment, even when the instrument is in the fully open position of FIG. 2, the cylindrical key 38 has a substantial engagement with the slots 40, 42 at a point 46 adjacent the center of the instrument. As the instrument is brought to the closed position of FIG. 3, increasingly greater lengths of key 38 are received by slots 40, 42, which is accomplished in a continuous smooth movement of minimum friction providing a heretofore unobtainable precision alignment between the mating halves.

An important feature of the present invention is that the key and slot arrangement maintains alignment of the needle point ends 12, 14 when in the open and closed positions, and in all intermediate positions therebetween. An important feature provided by the present invention is that the degree of alignment increases as the tips are drawn together, with the alignment being provided over very nearly the entire length of the instrument, if desired. As illustrated, alignment is provided over at least 75% of the length of the displaceable halves of the instrument. Further, the alignment provided is smooth in operation since it is accomplished by a key or elongated guide member having an exterior smooth rounded surface being received within complementary shaped smooth rounded recesses of the slots 40, 42. In the preferred embodiment, not only are the key 38 and slots 40, 42, complementary-shaped, they are also machined to close tolerances for precise interengagement. In particular, for an instrument approximately 6 inches long and 5/16 inches in diameter, the slots are precision milled to form matching semicylindrical key receiving slots. The key, made from slightly oversized cylindrical stock, is machined to within 0.5 mils (0.0005 inches) of the slot diameter. The half portions, 18, 20, are matching halves cut from a common blank preferably cut by a precision electrical discharge cutting machine, to complement the precision of the key and slots, thereby ensuring exact alignment of the needle tips, even under the 20× magnification typically employed during microsurgery. Thus, the halves are complementary and mated because they are cut from the same blank in contrast to the usual surgical tool in which the halves are formed from their own single blank and machined before being combined for the first time in the instrument. While differences in shape or size between blanks may not appear to be significant to the human eye without magnification, the differences in size or shape between the halves when under 20× magnification appear quite large and quite significant.

While the key 38 illustrated in the Figures is shown as a right circular cylinder, the term "cylinder" as used to describe the preferred embodiment of the present invention is used in its broader sense and includes shapes that are developed ellipsoids or developed conical shapes. It is even contemplated that the key 38 could be diamond-shaped, i.e., a square cross section turned on one edge. This latter embodiment contemplates a generally V-shaped slot for receiving its respective half portion of the aligning key. Also, the present invention contemplates a square cross-section key not turned on edge, but presenting one of its flat faces to a key-receiving slot.

As explained above, microinstruments of the type addressed by the present invention are frequently used in prolonged operations, and accordingly, any improved efficiency in manipulating the instrument is particularly advantageous. In this regard, the two mating halves 18, 20 are conveniently provided with a spring bias force which tends to maintain those halves in their open position. The spring bias force is provided by the material and configuration of the mating halves, and their joined end 22. In particular, the two mating halves 18, 20, are compressed together at the joined end 22 and one or both of the halves is slightly bent apart so that the material of that half portion is "set", whereby, upon closing the instrument, a spring bias force tending to open the instrument is generated. Of course, the material from which the mating halves 18, 20, are formed must be suitable for this purpose, i.e., must generate a bias force when deflected from its "set" or bent position. Numerous materials, particularly metallic materials illustrating these qualities, are known in the art. The preferred materials are titanium or 420 stainless steel, although injected molded plastic or die cast metal could also be used. In particular, heat treating to obtain the desired hardness (as will be described below), also imparts desirable spring bias characteristics to the titanium and stainless steel materials.

To further enhance this spring bias feature, so as to lessen and control the force required for closure of the instrument, cut-away window portions 48 are formed in each half portion 18, 20. The window portions 48 are also advantageous in reducing the overall mass of the instrument, a desirable feature in that fatigue experienced by a surgeon, especially during a lengthy operation, is significantly reduced. If necessary, further weight reduction can be accomplished by "over-sizing" portions of one or either slot 41, 42 to thereby remove more metal. Preferably, the oversizing will be done at the central location 46 of the slots 40, 42 so that here will always be guiding registration at the rear of the slots with the key 38 and with the tip portion of the slots and the key as the tips are brought together. It is to be understood that at least portions of the slots 40, 42 must be relatively close-fitting with the key 38 (as explained above) to provide the necessary alignment under 20× magnification.

To further aid in aligning the two mating halves 18, 20 and to provide a convenient, cost-effective assembly for the surgical instrument, closed ends 51 of the half portions 18, 20 are provided with external threads 50 as best seen in FIG. 8. When the half portions 18 and 20 were cut from the same blank, about 1/64 of an inch of metal was removed by the EDM machining and hence when the flat surfaces 28 and 30 are engaged, the thread portions 50 do not make a true cylindrical path for the mating thread 52 on the cap 24. To restore the cylindrical shape, a locator shim 53 is provided and placed into locator shim recesses 54 in wall 30 of each half 18 and 20. The locator recesses have top and bottom walls 55 which abut end walls 56 on the locator shim 53 which herein is the form of a flat, metallic plate sized to fit snugly in the recesses. The thickness of the locator shim is such that when the halves 18 and 20 are placed together with the locator shim in the recess, the threads 50 cooperate to provide a true cylindrical thread; and thus, in effect, replace the metal lost during the electrical discharge machining of the blank. Herein, the locator shim 53 is preferably mounted on the cylindrical key 38. Herein, the end of the key 38 is slitted or slotted at 57 and the slot 57 extends down to end wall 58 at the bottom of the slot and against which is abutted the lower end 56 of the locator shim. In the preferred embodiment, the threads 50 in the end portions and in the cap 24 are sufficiently fine to provide a precise axial alignment of one half portion relative to the other. Further, the threaded cap assembly allows simple and rapid substitution of the key 38.

As illustrated in FIGS. 1-8, cap 24 has a vacant, hollow portion 24a at its outer end. This provides an added length to the instrument but does not increase the weight of the instrument significantly if the cap is made from any number of lightweight well-known materials, such as aluminum, for example. With the key 38 fitted in the slots 40, 42 at opposite ends of the half portions 18 and 20 and with the locator shim 53 in the locator recesses 54 in each half portion, the cap 24 is threaded onto the axially and circumferentially aligned threads.

As mentioned above, portions of key 38 are always in engagement with the slots 40, 42, and a smooth, sliding action increases that engagement over the length of the key as the instrument is closed. If desired, an added degree of control can be provided by a protrusion 60 formed in half portion 20, mating with a complementary-shaped recess 62 formed in the other half portion 18. This feature provides transversely extending protrusions 60 straddling either side of key 38 adjacent its free end 38b.

To further enhance this control adjacent the free end of the key, a second axially-adjacent pair of protrusions and recesses can be provided. In the illustrated arrangement, a protrusion 64 is received in a complementary-shaped recess 66. Protrusion 64 is formed in half portion 18, immediately adjacent recess 62 so as to form a continuous S-shaped mating surface therewith. Similarly, the recess 66 is formed in half portion 20 immediately adjacent protrusion 60 to form a continuous complementary-shaped S-shaped mating surface. The two half portions are identical except for a reversal of the configuration of these S-shaped mating surfaces. Although the shapes of the protrusions and recesses illustrated in the Figures approximate a "square-wave" they can be rounded at their peaks and valleys to approximate a "sine-wave" configuration. Alternatively, the protrusions and recesses can be generally triangular in shape. It is desired, however, that the tips of the protrusions be tapered to ensure a smooth release of one S-shaped mating surface from the other when the instrument is opened. For example, the illustrated "square-wave" protrusion is preferably tapered to form a blunted point.

The protrusions 60 and 64 may provide a constant continual engagement with the key 38 at their respective slots 40, 42, it being appreciated that the interior surfaces 60a (FIGS. 5 and 6) on the protrusions extend vertically as continuous extensions of the side wall forming the slot 42. Likewise, interior surfaces 64a on the protrusions 64 extend vertically as extensions of the side walls of the slot 40 to engage the key 38 at all times. Thus, the interior surfaces 60a and 64a each engage opposite sides of the key 38 when the instrument is fully opened as well as when fully closed and at positions therebetween. The slots 40 and 42 may be machined oversized at areas indicated by lines 42c and 42d in FIG. 5 to reduce the weight of the instrument, because the interior surfaces 60a and 64a on the protrusions will still engage the bar 38 and maintain registration when the instrument is open as shown in FIG. 2. This reduced area of engagement, the oversized machined areas 40c and 40d, and also similar oversized machined areas about the slot 42 should lessen any frictional binding between the instrument halves and the key 38. If desired, the lateral dimension of the space between the protrusions of a given half portion can be tapered in an outward direction to provide a "funneling" of the key into the slot, either 40 or 42. However, in the preferred embodiment, any such tapering is not provided, such funneling not being required as the key is constantly contained within the protrusions of one of the half portions, and preferably is always contained within the protrusions of both half portions.

As illustrated in the detailed, exploded view of FIG. 8, further weight reduction can be obtained by fashioning key 38 from hollow, tubular stock. All other features of alignment, particularly the smooth exterior, smooth rounded surface of the key extending into the smooth, rounded surface of the slots, is maintained.

It will now be appreciated that FIG. 5, illustrating the half portion 20 would be identical to a similar view of the half portion 18, but for an interchanging of its protrusion 64 and recess 62. That is, the shear tip 12 would be identical to that illustrated for the shear tip 14 at FIG. 5, the slot 40 would be identical to the illustrated slot 42, and all remaining of the half portion are identical except for the interchanging of the positions of the protrusion 64 and recess 62.

When adapted as a scissors, the microsurgical instrument of the present invention permits extremely discrete cutting actions with precise finger pressure. However, the scissors instrument of the present invention is also fully compatible with other rotational neurosurgery techniques. For example, due to the extremely small angle formed at the tip of the scissors and the relatively long length of the tips, a scissors instrument constructed according to the present invention is useful not only for cutting tissue, but for the frequently associated tasks of spreading tissues and dilating vessels. Heretofore, it was necessary to employ different instruments for each of these tasks, thereby slowing progress of the operation.

With reference to FIGS. 10 and 11, the second illustrated example 110 of the invention will be described. The forceps 110 according to the present invention is especially useful for microscopic surgery. It will be appreciated that a fine curved microsurgical needle can be distorted if it is roughly handled and that once distorted, it can no longer be used. The needles are difficult to grip by those who are not highly trained in microsurgery; and when a surgeon makes numerous stitches in a microsurgical operation, it is to be understood that an occasional needle may pop out of the grasp of the instrument and be lost with the instruments heretofore used.

Typically, the microsurgeon with a conventional needle holder grasps the needle with his dominant hand, and with a forceps, such as shown in FIGS. 10 and 11 in his non-dominant hand, he then grasps a needle end with the forceps and rotates the needle point upward with the thread bearing end being likewise pointed upward. In this position, the needle point is ready to be rotated through a piece of tissue, such as a human vessel for anastomizing blood vessels together. Manifestly, the particular end uses of the microsurgical instrument of the present invention can vary considerably, and may take forms other than the scissors or forceps shown herein. Because the microsurgery may take hours to perform and involves numerous stitches, it is important that the instrument employed be designed to facilitate the work of the surgeon and to reduce his fatigue from use of the instrument. Microinstruments of the present invention are adapted for use with rotational microsurgical techniques and are particularly advantageous in this regard. Further advantages, especially when grasping curved needles, are provided in the needle holder described below with reference to FIGS. 12-14.

The central portion of the forceps 110 will have the same protrusions (such as the illustrated protrusions 60 and 64) and the same slots (40 and 42) and use the same key (such as the key 38). Because they already have been described, these keys, slots and protrusions will not be described again.

The tips 112 and 114 of instrument 110 have points or ends 112a and 114a, respectively, as sharp and as pointed as needles, and the movements thereof are only about 0.2 inches or 5 mm between opening and closing. The needles are so fine that if drawn to scale adjacent the points 112a or 114a the needles would appear only as a fine small line adjacent points 112a or 114a Movement of the needle as much as one inch moves the needle out of the field of view of the microscope; which typically provides 20× magnification. The points 112a and 114a of the instrument appear as needle sharp points to the naked eye and they usually are only in the range of 50 microns to 2 mm in diameter, and form an angle of only a few degrees at their tip. Because the points 112a and 114a are so fine and sharp, any deflection laterally, i.e., a twisting movement of only a few millimeters causes problems in properly gripping the needle. Since the points 112a and 114a are often five or six inches from the tip ends, the points have a long unsupported length that can lead to such deflections particularly when the surgeon is twisting the instrument, a maneuver frequently practiced in rotational microsurgery techniques.

Because the points 112 and 114 on the ends of the microsurgical instrument 110 (FIGS. 10 and 11) are so sharp, great precision of the planar closing movement is needed, more than with the macrosurgical tools of the prior art, especially since the microsurgical instrument is used under a 20° microscope. The alignment features, particularly the interengagement between key and slots of this embodiment, are the same as described above in FIGS. 1-8.

As has been described, the preferred instrument shape is substantially cylindrical when the halves 118, 120 are brought together, so that the instrument may be rotated about its longitudinal axis. More specifically, the cylindrical central section of the instrument is laid along the middle finger of a hand resting on a surface to suppress tremors, and the thumb is rotated along the cylindrical surface to impart a spindle-like rotation to the instrument along its longitudinal axis on the middle finger thereby turning the tips through a natural arc of rotation to move a needle thread, etc. with a precise controlled movement. In the preferred embodiment illustrated in FIG. 1, finger texturing is provided to assist the surgeon in maintaining precise control of the instrument, even while wearing conventional gloves adapted for surgery. Rather than employ the familiar knurling, finger texturing is provided by a series of spaced-apart cylindrical grooves 65 machined into the outer surface of the cylindrical body of the instrument. The finger texture grooves 65 are located at the location where the surgeon will grip the tool for turning and provide a non-slip surface. These spaced-inward grooves offer significant improvement over knurling in that the surgeon's gloves are not snagged or degraded by contact with the finger texturing, while an improved tactile engagement with the instrument is provided. The texturing is not shown in all figures for purposes of clarity. However, the preferred embodiments do, in fact, employ such texturing.

As pointed out above, the tips of the various embodiments of the instrument are very fine, and easily damaged. Accordingly, there is provided an arrangement for a removable and replaceable tip 114b as shown in FIGS. 17 and 18. The tip has a rectangular extension 170 at one end which fits into a slot 171 formed in the half portion 120. The slot 171 is rectangular in cross-section to prevent rotation of the tip. The associated tip would have a similar extension which would fit into a similar groove in the other half 118. Spring loaded balls 172 project from each side 173 of extension 170 and when seated onto the associated depressions 174 in the half 120 at the slot 171 lock the tip in place. Other locking means, such as lock screws, roll pins, push button releases and the like could be used. End walls 175 on the tip are held in tight engagement with end walls 176 on the cylindrical portion when the tip is detented in. position. The slot 142 preferably extends into the replaceable tip 114b.

Attention will now be directed to a method of making the surgical instruments described above. It is important from a commercial perspective that an economical method of making precise interchangeable parts be provided. An inventive method satisfying these requirements will now be described. In the preferred method of manufacture, a blank having a generally cylindrical body of titanium or 420 stainless steel is provided. The blank is cut by electrical discharge cutting means as are known in the art. In the preferred method, the cutting operation is computer-controlled, and is performed principally by translating the cylindrical blank relative to the electrical discharge cutting means, which is aligned to travel from end to end along the axis of the blank. Immediately prior to this cutting step, the long, needle-like tapered tip is machined at the leading end of the blank so as to provide a working tip for the instrument. Also, the thread 50 and the finger texture grooves 65 are machined onto the blank before it is split in half. The preferred angle for each semiconical tip surface is 5° to give the typical surgeon the proper length of tip point from his fingers located at the textured grooves 65. A 4° taper provides a shorter, stubby point. Also preparatory to the cutting step, the other, closed end is threaded to form the threaded portions 50; and a series of special finger texture grooves 65 (FIG. 1) are cut in circular shape and spaced longitudinally of each other on the outer cylindrical surface of the blank. If desired, the finger texture grooves may be extended down into the conical surface so that surgeons with a shorter finger grip may also grasp a textured surface. These preliminary operations having been performed, the cylindrical blank is moved relative to the electrical discharge means such that the two half portions are continuously cut from end to end. The windows 48 are also cut into the blank by the electrical discharge machining operation.

The cutting tips can be hardened to retain their sharpness. For example, the 420 stainless material provides a tool having a 52 Rockwell hardness. As an alternative, titanium can be vapor deposited on the flat surfaces 12a, 14a, and the cutting edges 12c, 14c to further enhance wearability, and to obtain a 54 Rockwell hardness as measured on the "C"-scale. Other coating materials and hardening processes available today may also be used. After hardening, the two half portions are laid open and a precise milling operation is performed on each half portion to form the slots 40 and 42 therein. The slots 40 and 42 are precisely milled into the faces 30 and additionally, as best seen in FIG. 5, other metal is removed about the slots 40 and 42 on opposite sides of the protrusions and recesses until the tool is at the precise weight desired to form the oversized areas 42c and 42d. The locator shim recesses 54 are also machined into each half. If the tool halves are made from a relatively soft material, such as injected plastic or die cast metal, usable surfaces at the cutting tips or other portions subject to wear may be provided by atomic deposition of titanium or any of the like commercially available coatings, after the half portions are formed and finished, as above.

In practice, the width of material removed by the electrical discharge cutting apparatus is well known and carefully controlled throughout the cutting steps. In order to regain a precise cylindrical configuration for the thread 50, the locator shim 53 having a width to compensate for the width of the electrical discharge cut is placed into the recesses 54 (FIG. 8) and the key 38 is placed into the slots 40 and 42. The cap 24 is then threaded onto threads 50 which are aligned in the axial direction by the shim.

The preferred key 38 is a precision sized tube that has its outer wall oversized and then the tube exterior wall is centerless ground to provide a precise cylindrical surface of constant diameter throughout its length. A slot 57 is machined into one end of the key to receive the locator shim 53.

The method of forming the surgical scissors is somewhat more complicated in that the scissors must be provided in the cutting operation. The cutting by the EDM apparatus preferably starts at the forward conical tip. When the penetration of the cutting arrives at the point of the shoulders 28a, 30a, the cylindrical blank is rotated or is generally spirally or helically displaced 90° in a counterclockwise direction (observed from the sharpened conical tip) and cutting along the axis of (now rotated) blank proceeds until the point of formation of the recesses 62, 66 and protrusions 60, 64 is approached. At this point, the blank is moved transversely of its axis in a first transverse direction and upon a slight additional axial displacement, the tip of a protrusion and a valley of a recess is formed. The blank is then displaced in an opposite transverse direction past the axis of the blank so that not only is the first set of protrusions and recesses completed, but the formation of the latter, downstream set of protrusion and recess configurations is initiated. A further slight axial displacement forms the peak and valley of the protrusion and recess. A final transverse displacement of the blank is performed until the electrical discharge cutting means is again aligned with the axis of the blank. The cut then proceeds along the axis of the blank until its reaches the area at which the windows 48 are to be cut. The cutting operation proceeds as before, and a loop cut is made to cut the window 48 from the metal blank and then the thread 50 is severed and then the two half portions are completely separated, one from another.

To form the spring biased halves, the half portions are placed in a fixture and each is bent to a 10° angle at the thin window 48 sections so that tips are spaced 20° apart in their open position: manifestly, this degree of opening may be varied. The illustrated EDM gap or slot is about 0.015 inches, and to bring the scissor flat cutting faces 12 and 14 back into tight engagement, the halves are placed in a fixture and the halves are permanently deflected with the faces 12 and 14 in tight engagement and parallel to each other. Thus, the cutting edges 14c and 14d will likewise be closely adjacent to provide a tight shearing action.

The precision bores 40 and 42 are not drilled into the stock, as a drill might wander and not provide the precision desired. Herein, it is preferred to hold the tolerances for these bores to about 0.0001 inch and likewise to centerless grind the key 38 to a similarly small tolerance dimension to assume the accurate registration of the matched halves each cut from the same piece of stock.

Thus, it will be seen that the microsurgical tool may be formed with separate and replaceable tip and spring members which may be quickly detached from their respective holder bodies if a tip becomes damaged or if it is desired to use a different type of tip in the holder bodies.

It will now be appreciated that the above-described microsurgical instrument provides a unique alignment arrangement which maintains a precise fit of the instrument tips at all times, a feature which is essential to the delicate work of a microsurgeon. Further, with instruments constructed according to the present invention the surgeon can employ rotational techniques which offer improved precision and control while facilitating the use of both dominant and non-dominant hands throughout the course of delicate surgical maneuvers.

When utilized to provide a needle holder, the microsurgical instrument of the present invention provides improved setting of the surgeon's needle. The needles used in microsurgery to sew blood vessels together are curved, and are typically so small that they are difficult to see without magnification. Further, when these curved needles are grasped by conventional micro-needle holders, they frequently fall out of the jaws of the instrument or turn in an unintended direction. This requires the surgeon to employ a forceps in his non-dominant hand to bring the needle into the proper position. It will be appreciated that, throughout a lengthy operation, the constant repetition of this awkward and time-consuming two-handed technique is particularly undesirable. When configured as a needle holder, the microsurgical instrument of the present invention provides continuous engagement of the needle in the jaws or working area of the instrument, and maintains the rotational movement of the needle relative to the instrument, thereby automatically bringing the needle into proper position for suturing.

Turning now to FIGS. 12-16, two alternative embodiments of needle holders constructed according to the present invention are illustrated. The needle holders have major body portions substantially identical to those of the forceps and scissors instruments described above. For example, each needle holder has two mating halves aligned with an internal key in their open and closed positions, and at all intermediate positions therebetween. In addition, the needle holders are conveniently provided with complementary mating protrusions and recesses, one on each body half-portion, to provide further alignment between the halves, as described above. FIGS. 12, 13 and 13a illustrate a needle holder of curved configuration, and the needle holder of FIGS. 14, 14a, 15 and 16 has a straight, or conoid outer configuration. In either alternative embodiment, curved, mating jaw portions provide improved control when grasping micro-needles.

Referring to the first, curved alternative embodiment, the pointed needle-grasping jaws of the instrument 210 of FIG. 12 are shown in the enlarged illustrations of FIGS. 13, 13a. The curved jaws comprise a portion of the interengaging tips 212,214 each of which extend from a respective body half portion 218,220 of the needle holder instrument 210.

FIG. 14 illustrates the second alternative, a "straight" configuration wherein conoid tips 312,314 extend from substantially identical half body portions, such as the body portions 218,220 of FIG. 12. FIGS. 14a, 15 and 16 are enlarged views of the curved jaw portion of FIG. 14 located adjacent the free ends of the tips.

Engagement between the mating tips of the straight configuration of FIGS. 14-16 will be described first, it being realized that the arrangement of the tips of FIGS. 12-13a may be thought of, at least conceptually, as being formed by a gross bending of the instrument tips of FIGS. 14-16, with care being taken to compensate for the adjustment in length of the mating tips 212,214 caused by such bending.

Referring now to FIGS. 14-16, the mating tip portions 312,314 having curved, mating jaw-like surfaces 312a,314a formed by a precision, computer-controlled EDM cutting operation which cuts a solid conoid blank, as described above with respect to the other embodiments. In one of its aspects, the present invention provides curved mating surfaces 312a,314a composed of accurate portions, the centers of which lie to one side of the instrument axis. The EDM cutting operation does not intersect the central or axial free end 320 of the instrument. Rather, cutting of the instrument blank is initiated at one side of the axial free end. Cutting follows a curved plane perpendicular to the instrument axis, to form curved mating surfaces 312a,314a that are simple curved surfaces and are not compound or complex curved surfaces as would be formed by twisting the instrument blank about its axis as the EDM cutting operation advances from one end of the blank to the other. As a result, tip portion 314 is longer than portion 312 and has a generally hooked-shape which overlies or completely covers the mating surface 312a of the other tip portion 312. The mating tip portions 312,314 form a slightly truncated conoid shape when mated.

With reference to the enlarged view of FIGS. 14a, 15 and 16, the shorter tip portion 312 and the longer tip portion 314 are formed to provide an intimate engagement over a working area 324 extending between the free ends 332,334 of the tip portions and a reference point 340 (see FIG. 15) remote from the instrument tip. A small gap 344 between the body portions extends from reference point 340 to the opposite end of the instrument (not shown) where the half portions are connected together, as by the threaded cap 24 described above with reference to FIG. 1. By way of example only, in one preferred embodiment, a needle holder instrument has an outside diameter of 0.32 inches along its cylindrical major body portion, and has a sharpened or conoid tip measuring 1.61 inches in an axial direction. The reference point 340, defining one end of working area 324, is located 0.160 inches in an axial direction, from tip 320 of the needle holder instrument. The radius of curvature of the mating surfaces 312a,314a is approximately 0.03 inches, and is offset 0.026 inches in an axial direction from the tip 320. The working area 324, as described above, is 0.160 inches or 4 millimeters in axial length and is characterized by an intimate engagement between the mating surfaces 312a,314a. In a preferred embodiment, the mating surfaces of the working area are provided with a series of serrations extending, with reference to FIG. 14, into the plane of the paper and have a depth ranging between one-half to one mil. Needles are preferably grasped in the anterior, curved portion or jaw of the working area, but may also be grasped in the straight, posterior portion of working area 324.

The working area 324 and particularly the curved jaw portions 312a,314a thereof are extremely small, the entire working area comprising only approximately 10% of the axial length of the conoid tip of the instrument. If the conoid tip were fully developed so as to terminate at an infinitely sharp point, its axial length would be approximately 1.8 inches long, beginning at a base of 0.32 inches diameter where the conoid tip is joined to the remaining cylindrical body portion of the instrument. The preferred embodiment, as mentioned, is slightly truncated, with the instrument tip having a length of 1.61 inches.

Returning now to FIGS. 12, 13 and 13a, tip portions 212,214 are substantially identical to tip portions 312,314 discussed above, but for a bending of those portions along a common one inch radius, located approximately 1.2 inches in an axial direction from the base of the conoid tip. All other features of the tips 212,214 remain the same as described above for tips 312,314. For example, the curved surfaces 212a,214a each have a 0.03 inch radius located approximately 0.026 inches posterior of the instrument tip 220. As with the aforementioned "straight" embodiment, the curved portions 212a,214a form complementary-shaped inter-engaging accurate surfaces, with the free end of the longer tip portion, namely, tip portion 214, overlying the free end of tip portion 212. As illustrated, the centers of curvature of the surfaces 212a,214a lie on the same side of the instrument, as does the one inch radius of curvature of the tip portions 212,214.

In addition to providing the same improved needle-gripping features as the embodiment of FIGS. 14,15, the curved embodiment of FIGS. 12,13 increases the surgeon's field of view for positions of the instrument commonly held during surgery. Also, it will be appreciated, that, when using the rotational technique described above, the tips of the straight and curved alternative embodiments of the needle holder will sweep different paths, each having their own distinctive advantages in the course of a microsurgical procedure.

The foregoing description and drawings merely explain and illustrate the invention and the invention is not limited thereto, except insofar as the appended claims are so limited. Those who are skilled in the art and have the disclosure before them will be able to make modifications and variations therein without departing from the scope of the invention.

What is claimed is:

1. A hand-held microsurgical tool for use in microsurgery, said tool comprising:
    an elongated body including a cylindrical section having a longitudinal axis about which the body may be rotated by a surgeon;
    said cylindrical section comprised of first and second generally opposed, coextensive longitudinally extending portions joined at a closed end;
    needle point ends on each of said first and second portions located opposite from the closed end and movable toward and away from each other between closed and open positions, respectively; and
    alignment means for maintaining alignment of the needle point ends when in the open and closed positions and at all intermediate positions therebetween, said alignment means comprising an interior guide member having a surface in sliding engagement with at least one of said first and second portions, said guide member being located within the configuration of the cylindrical section so as not to interfere with the rotation of the cylindrical section of the tool.

2. A microsurgical tool in accordance with claim 1 in which at least the other of said first and second portions defines a recess complementary shaped to receive said guide member so as to allow mating engagement between the tips of said first and second portions when said portions are in said closed position.

3. A microsurgical tool in accordance with claim 2 in which said guide member comprises a generally semicylindrical member receivable in said complementary-shaped recess.

4. A microsurgical tool in accordance with claim 2 in which said guide member comprises a cylindrical member, and each said first and second portions define recesses for receiving said cylindrical member.

5. A microsurgical tool in accordance with claim 2 in which at least one of said portions defines a generally transverse protrusion and the other of said portions defines a complementary-shaped recess for receiving said protrusion.

6. A microsurgical tool in accordance with claim 5 in which the other of said first and second portions includes a generally transverse protrusion receivable in a complementary-shaped recess defined by said one portion.

7. The microsurgical tool of claim 6 wherein the protrusions and recesses of each portion are immediately adjacent each other so as to form a single continuous mating surface for the other portion.

8. A microsurgical tool in accordance with claim 1 in which said first and second portions each have semiconical tips thereon extending between the cylindrical portion and the needle point ends.

9. A microsurgical tool in accordance with claim 1 in which shearing edges are formed on said needle point ends facing each other to make a scissors cut.

10. A microsurgical tool in accordance with claim 1 including means for detachably mounting the needle point ends on said portions for replacement thereof with other ends.

11. A microsurgical tool in accordance with claim 1 further comprising a finger texturing means comprising a plurality of spaced-apart grooves inwardly extending from an outside surface of said body.

12. A microsurgical tool in accordance with claim 1 wherein said needle point ends have free ends and complementary-shaped interengaging accurate surfaces, with one needle point end overlying the free end of the other needle point end, so as to form a working area between the needle point ends for grasping and manipulating a microsurgical needle.

13. A hand-held microsurgical scissors for use in microsurgery, said scissors comprising:
    an elongated body including a central cylinder portion having a longitudinal axis about which the body may be rotated by a surgeon;
    means on said first and second portions on said elongated body being joined at a closed end;
    semiconical pointed ends on each of said first and second portions located opposite from the closed end and movable between toward and away from each other and closed and open positions, respectively for cutting;

cutting edges on each of said semiconical ends for cutting tissue placed therebetween; and alignment means for maintaining alignment of the semiconical ends and the cutting edges when cutting tissue, said alignment means maintaining alignment of the semiconical ends when in the open and closed positions and at all intermediate positions therebetween, said alignment means being located within the configuration of the body and so as not to interfere with the rotation thereof.

14. A microsurgical tool in accordance with claim 13 in which said means joining the sections together comprises an internally threaded member threadably joining the portions together.

15. A hand-held microsurgical scissors for use in microsurgery, said scissors comprising:

an elongated body including a central cylinder portion having a longitudinal axis about which the body may be rotated by a surgeon;

first and second opposed portions of said elongated body lying on either side of a first plane and extending generally parallel to said axis;

means for hingedly joining first ends of said portions together;

opposed axially-extending semiconical scissors blades lying on either side of a second plane generally normal to said first plane and carried on second ends of respective opposed portions so as to be movable toward and away from each other between closed and open positions, respectively, said scissors blades defining a needle-like tip when in said closed position;

cutting edges on each of said scissors blades for cutting tissue placed therebetween; and alignment means for maintaining alignment of said scissors blades and said cutting edges when cutting tissue, said alignment means located within the configuration of the body so as not to interfere with the rotation thereof.

16. The scissors of claim 15 wherein said elongated body includes a truncated conical portion joining said needle point ends to said central cylindrical section so as to form a continuous outer surface over the length of said scissors.

17. A hand-held microsurgical tool for use in microsurgery, said tool comprising:

an elongated body including a cylindrical section having a longitudinal axis about which the body may be rotated by a surgeon;

said cylindrical section comprised of first and second generally opposed, coextensive longitudinally extending portions joined at a closed end;

needle point ends on each of said first and second portions located opposite from the closed end and movable toward and away from each other between closed and open positions, respectively, said needle point ends having free ends and complementary-shaped interengaging accurate surfaces, with one needle point end overlying the free end of the other needle point end, so as to form a working area between the needle point ends for grasping and manipulating a microsurgical needle; and alignment means for maintaining alignment of the needle point ends when in the open and closed positions and at all intermediate positions therebetween, said alignment means comprising an interior guide member having a surface in sliding engagement with at least one of said first and second portions, said guide member being located within the configuration of the cylindrical section so as not to interfere with the rotation of the cylindrical section of the tool.

18. The microsurgical tool of claim 17 wherein said needle point ends when closed generally comprise a cone.

19. The microsurgical tool of claim 17 wherein said needle point ends comprise a cone which is formed so that its axes lies along a curved line.

20. A hand-held microsurgical tool for use in microsurgery, said tool comprising:

an elongated body including a central cylindrical section having a longitidinal axis about which the body may be rotated by a surgeon;

finger-texturing means on at least a part of said central cylinder portion comprising a plurality of spaced-apart grooves inwardly extending from an outside surface of said body;

said central cylindrical section comprised of first and second generally opposed, coextensive longitudinal portions joined at a closed end;

needle point ends on each of said first and second portions located opposite from the closed end and movable toward and away from each other between closed and open positions, respectively;

mating projection and recess members carried on respective ones of said first and second portions so as to be movable toward and away from each other as said portions are moved between said closed and said open positions, respectively;

alignment means for maintaining alignment of the needle point ends, said alignment means maintaining alignment of the needle point ends when in the open and closed positions and all intermediate positions therebetween, said alignment means comprising an interior elongated guide member having an exterior smooth rounded surface and extending into said central cylindrical section and received in at least one of said first and second portions so as to be located within the configuration of the central cylindrical section and so as not to interfere with the rotation of the central cylindrical section of the tool.

* * * * *